United States Patent
den Hoed

(10) Patent No.: US 10,301,374 B2
(45) Date of Patent: May 28, 2019

(54) METHOD OF PRODUCING COLLAGEN FROM HYDROLYZED EGG MEMBRANE

(71) Applicant: Robert den Hoed, Sioux Center, IA (US)

(72) Inventor: Robert den Hoed, Sioux Center, IA (US)

( * ) Notice: Subject to any disclaimer, the term of this patent is extended or adjusted under 35 U.S.C. 154(b) by 41 days.

(21) Appl. No.: 15/719,042

(22) Filed: Sep. 28, 2017

(65) Prior Publication Data

US 2018/0016321 A1     Jan. 18, 2018

Related U.S. Application Data

(63) Continuation-in-part of application No. 13/913,870, filed on Jun. 10, 2013, now abandoned.

(51) Int. Cl.
| | |
|---|---|
| *C12P 21/06* | (2006.01) |
| *C07K 14/78* | (2006.01) |
| *A23L 29/281* | (2016.01) |
| *A61K 31/7008* | (2006.01) |
| *A61K 38/47* | (2006.01) |
| *A61K 31/737* | (2006.01) |
| *A61K 38/39* | (2006.01) |
| *A61K 38/40* | (2006.01) |
| *A61K 31/728* | (2006.01) |

(52) U.S. Cl.
CPC ............ *C07K 14/78* (2013.01); *A23L 29/281* (2016.08); *A61K 31/7008* (2013.01); *A61K 31/728* (2013.01); *A61K 31/737* (2013.01); *A61K 38/39* (2013.01); *A61K 38/40* (2013.01); *A61K 38/47* (2013.01)

(58) Field of Classification Search
CPC ...................................................... C12P 21/06
See application file for complete search history.

(56) References Cited

U.S. PATENT DOCUMENTS

| | | | | |
|---|---|---|---|---|
| 2009/0104173 A1* | 4/2009 | Strohbehn | .............. | A61K 38/39 424/94.61 |
| 2013/0224830 A1* | 8/2013 | Tanaka | .................. | A61K 35/57 435/189 |

FOREIGN PATENT DOCUMENTS

| | | | | |
|---|---|---|---|---|
| WO | WO-2012029529 A1 * | 3/2012 | ............. | A61K 35/57 |

OTHER PUBLICATIONS

Chen et al., "Physicochemical properties of alkaline serine proteases in alcohol," J Protein Chem 14(4):205-215, 1995.*

* cited by examiner

*Primary Examiner* — Rosanne Kosson
(74) *Attorney, Agent, or Firm* — Zarley Law Firm, P.L.C.

(57) ABSTRACT

A method of producing collagen from hydrolyzed egg membrane includes combining 95% ethanol, cold water, a bacterial pH neutral protease and/or an alkaline bacterial protease, a pH neutral bacterial metalloendopeptidase, sodium bisulfite, and egg membrane. Once combined, the solution is mixed slowly and then heated to a desired pH range and temperature. Once a desired temperature is reached, the heated solution is set aside to digest for a prolonged period of time. Next, the digested solution is centrifuged and collected to form a filtered solution. Finally, the filtered solution is spray dried and packaged.

10 Claims, 2 Drawing Sheets

METHOD OF PRODUCING COLLAGEN FROM HYDROLYZED EGG MEMBRANE

CROSS REFERENCE TO RELATED APPLICATION

This application is a continuation in part of application Ser. No. 13/913,870 filed Jun. 10, 2013.

BACKGROUND OF THE INVENTION

This invention is directed to a method of producing collagen from hydrolyzed egg membranes and more particularly to producing collagen from hydrolyzed egg membrane having lysozyme, ova transferrin, and sialic acid (LOS).

Eggshell membranes are well known as a source of valuable bioactive materials, including collagen, that have widespread applications in medical, health, and cosmetic industries for joint and wound healing and skin care. To date, a major drawback to their use has been the difficulty in solubilizing these materials in a sufficiently stable and active pure form at an industrial scale so that high yield is achieved in an economic manner without using caustic solvents.

The amount of detectable and usable collagen type protein solubilized from the starting material by known processes is low, the techniques are not cost-effective, and often the recovered protein components do not maintain their native activity—i.e., they are not as stable as commercialization demands. Therefore an inexpensive process for producing collagen type protein from hydrolyzed egg membranes while maintaining both yield, purity and activity of the solubilized collagen type protein is needed, particularly one suited for commercial scale implementation.

An objective of the present invention is to provide a method of solubilization of egg membranes and collagen type protein extraction under chemically neutral conditions without the use of caustic solvents.

A further objective of the present invention is to produce an improved collagen through a method that uses hydrolyzed egg membranes.

These and other objectives will be apparent to one of ordinary skill in the art based upon the following written description, drawings, and claims.

SUMMARY OF THE INVENTION

A method of producing collagen from hydrolyzed egg membrane includes combining 95% by volume ethanol, cold water, a pH neutral bacterial protease and/or alkaline bacterial protease, a pH neutral bacterial metalloendopeptidase such as 14L®, sodium bisulfite, and egg membrane. Once combined, the solution is mixed slowly and then heated to a desired pH range. Once a desired temperature is reached, the heated solution is set aside to digest for a prolonged period of time. Next, the digested solution is centrifuged and filtered. Finally, the filtered solution is spray dried and packaged.

DETAILED DESCRIPTION OF THE PREFERRED EMBODIMENTS

Figure 1:
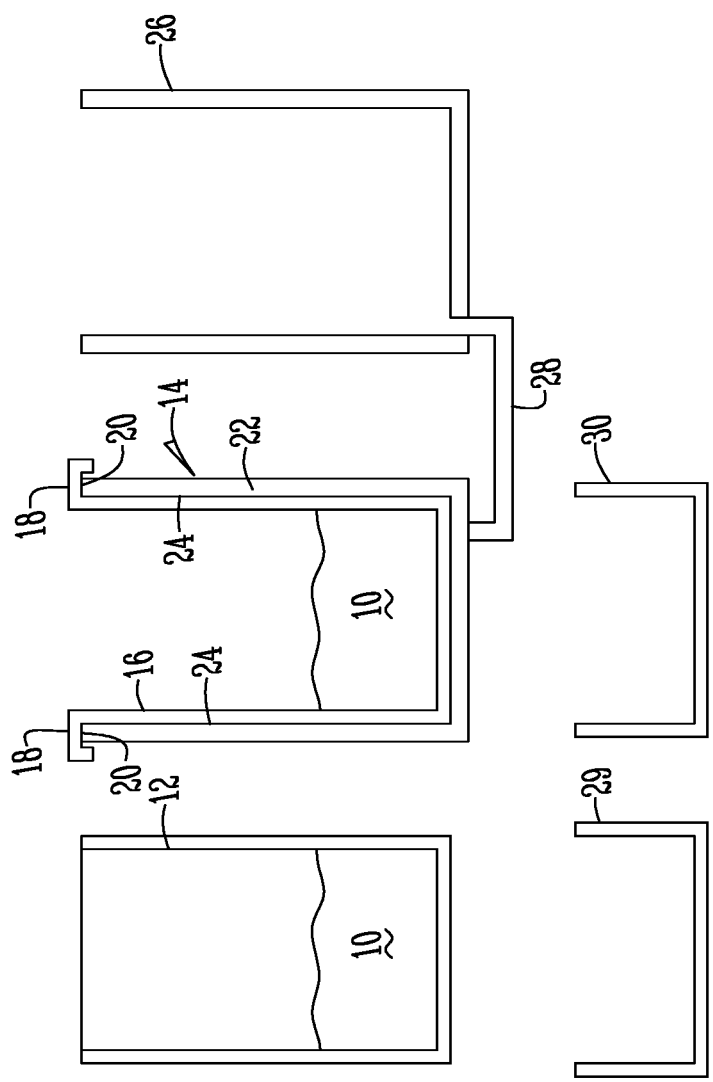
FIG. 1 is a schematic diagram of the environment of performing a method of producing collagen from hydrolyzed egg membranes.
Figure 2:
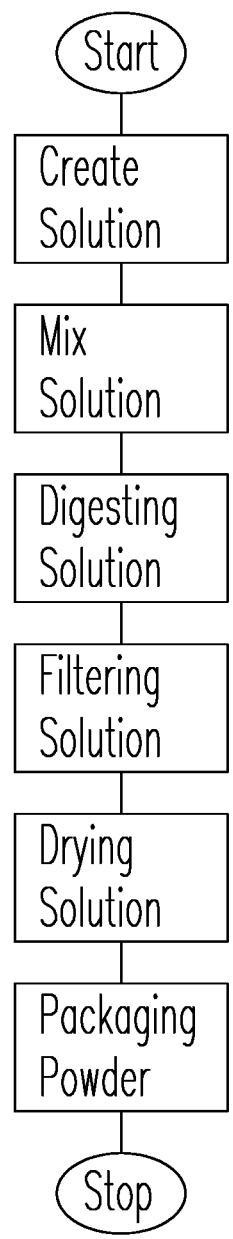
FIG. 2 is a flow diagram of a method of producing collagen from hydrolyzed egg membranes.

A method of making collagen from a hydrolyzed egg membrane includes the step of creating a solution 10 by combining 95% by volume ethanol, cold water, a pH neutral bacterial protease, and/or an alkaline bacterial protease, a pH neutral bacterial metalloendopeptidase, such as 14L®, sodium bisulfite, and dried or moist egg membrane. In this embodiment, ethanol in combination with sodium bisulfite, rather than methanol or amino acid-type alcohols, best removes the sulfates and chondroitins while unfolding the collagen type protein, breaking the disulfide bonds within the membrane material to form singular bonding chains that allow more efficient digestion of the membrane material by the preferred proteases at a neutral digestion pH. The neutral bacterial protease is preferably Neutralase®. Additionally, the alkaline bacterial protease is preferably an Alcalase® or L-660®.

The combination of neutral proteases under pH neutral conditions provides for partial hydrolysis of the collagen type protein within the membrane material rather than complete denaturation of the collagen type substrate protein within the membrane material caused by basic or caustic solvents or conditions. This partial hydrolysis results in retention of fragile hyaluronic acid and mucopolysaccharides otherwise destroyed or rendered undetectable by use of basic or caustic solvents and conditions. Hyaluronic acid has been shown to improve human skin and joint conditions including cancers, inflammation, granulation, wound repair (in both adult and fetal wounds), and cell migration.

As used herein, the term 14L® refers to a thermostable bacterial neutral metalloendopeptidase derived from a selected strain of *Geobacillus* species that is effective in a pH range of 4.0 to 10.0 and at a temperature between 35 and 80 degrees Celsius. Additionally, as used herein, the term L-6606 refers to an alkaline protease enzyme preparation derived from *Bacillus licheniformis*. The preparation is an endopeptidase used for hydrolyzing proteins and is effective in pH range of 7.0 to 10.0 and a temperature range of −1 to 21 degrees Celsius.

In a preferred embodiment the combined solution includes 750 ml of 95% ethanol, the addition of cold water to a 15 liter mark, 90 mls of an alkaline bacterial protease, 30 mls of pH neutral bacterial metallopeptidase, 36 grams of sodium bisulfate, and 1500 grams of egg membrane. The use of a neutral bacterial metalloendopeptidase, such as 14L®, results in better, more complete extraction of mucopolysaccharides from the membrane material and has the capacity to remain effective in the partial hydrolysis process unlike common, non-metallo, endopeptidases, for example, trypsin or pepsin. The use of the particular enzymatic combination above also improves current processes because it does not include animal based enzymes, such as trypsin, or alpha which have been found to be effective only in high temperature ranges, unlike the preferred combination which can perform in a range of temperatures, and to result in low retention of collagen type protein, mucopolysaccharides, and hyaluronic acid.

Additionally, neutral bacterial metalloendopeptidase is most effective when the collagen type substrate protein has been partially denatured or unfolded. Here, the ethanol and sodium bisulfite position the neutral bacterial metalloendopeptidase in its most effective state by unfolding the membrane material having the collagen type substrate protein into a more linear structure that is better hydrolyzed by the neutral bacterial metalloendopeptidase.

Once combined, the solution 10 is mixed slowly such that digestion of the membrane material occurs consistently within a mixing vessel 12 and heated to 60 degrees Celsius such that the solution 10 reaches a pH level between 4.0 and 10.0 pH. Preferably the solution 10 is mixed in a jacketed tank so that the solution 10 can be heated.

Once the temperature of the solution 10 reaches 60 degrees Celsius, the solution 10 is set aside and left alone in order to permit the solution 10 to digest for a period of between two to forty-eight hours. After digesting, the solution 10 is added to a centrifuge device 14 where the solution 10 is centrifuged at 2,000 rpm for five minutes. Once centrifuged, the filtered solution is pumped into a holding tank 26 through a discharge tube 28 of the centrifuge device 14. From the holding tank 26, the filtered solution is pumped to a sprayer 29 where the filtered solution is spray dried. The resulting collagen powder is then transferred to a drum 30 for packaging and distribution. The collagen powder retains a maximum amount of mucopolysaccharides and hyaluronic acid derived from egg membrane allowed by the combination of a neutral bacterial protease and/or alkaline bacterial protease, a neutral bacterial metalloendopeptidase, and sodium bisulfite.

Particularly, the dried filtered solution which results in a collagen powder has a minimum of 20% protein, 1.0% calcium, 2% ova transferrin, 2% lysozyme, 0.1% sialic acid, 0.1% hyaluronic acid, 1% mucopolysaccharide, and 0.1% chondroitin. In addition, the collagen powder preferably includes a minimum of 31.23% wt of mucopolysaccharide, a minimum of 35.4% wt chondroitin sulfate sodium, a minimum of 5.985% wt of hyaluronic acid, and a minimum of 5.337% wt of glucosamine$_6$. Further, preferred is a collagen powder having a molecular weight of 10 to 200 Kda. Thus, a method of solubilazation of egg membrane under neutral conditions without caustic solvents has been disclosed that, at the very least, meets all the stated objectives.

What is claimed:

1. A method of producing collagen powder from hydrolyzed egg membranes, comprising the steps of:
   a) providing a solvent that is 95% alcohol by volume:
   b) creating a solution by combining the alcohol solvent, water, at least one of a pH neutral bacterial protease and an alkaline bacterial protease, a pH neutral bacterial metalloendopeptidase, sodium bisulfite, and egg membrane, wherein the alcohol solvent and water are combined at 750 mL of the alcohol solvent to 14.25 L of water:
   c) mixing and heating the combined solution to a temperature of 60 degrees Celsius;
   d) digesting the solution for a period of between 2 and 48 hours;
   e) filtering the solution through a centrifuge device; and
   f) spraying the solution dry.

2. The method of claim 1 wherein the combined solution includes 750 mLs of the alcohol solvent, 15 liters of water, 90 mLs of a solution of the alkaline bacterial protease, 30 mLs of a solution of the pH neutral bacterial metalloendopeptidase, 36 grams of sodium bisulfite, and 1500 grams of egg membrane.

3. The method of claim 1 wherein the heated solution has a pH level of between 4 and 10 pH.

4. The method of claim 1, wherein the collagen powder comprises at least 20% protein, at least 1.0% calcium, at least 2% ova transferrin, at least 2% lysozyme, at least 0.1% sialic acid, at least 0.1% hyaluronic acid, at least 0.1% mucopolysaccharide, and at least 0.1% chondroitin.

5. The method of claim 4 wherein the collagen has a molecular weight between 10 and 200 Kda.

6. A method of producing collagen powder from hydrolyzed egg membranes, comprising the steps of:
   (a) creating a solution by combining 750 mLs 95% alcohol, 14.25 L water, at least one of a pH neutral bacterial protease and an alkaline bacterial protease, a pH neutral bacterial metalloendopeptidase, sodium bisulfite, and egg membrane;
   (b) mixing and heating the combined solution to a temperature of 60 degrees Celsius such that the pH reaches between 4.0 and 10.0;
   (c) digesting the solution for a period of between 2 and 48 hours;
   (d) centrifuging the solution; and
   (e) drying the solution to obtain the collagen powder, wherein steps (a)-(e) are completed in order.

7. A method of producing collagen powder from hydrolyzed egg membranes, comprising the steps of:
   (a) creating a solution by combining 750 mLs of a solvent that is 95% alcohol by volume, 14.25 L of water, 90 mLs of a solution of an alkaline bacterial protease, 30 mLs of a solution of a pH neutral bacterial metallopeptidase, 36 g of sodium bisulfite, and 1,500 g of egg membrane;
   (b) mixing and heating the combined solution to a temperature of 60 degrees Celsius such that the pH reaches between 4.0 and 10.0;
   (c) digesting the solution for a period of between 2 and 48 hours;
   (d) centrifuging the solution; and
   (e) drying the solution to obtain the collagen powder, wherein steps (a)-(e) are completed in immediate sequence.

8. The method of claim 7 wherein the alkaline bacterial protease is derived from *Bacillus licheniformis*.

9. The method of claim 7 wherein the neutral bacterial metallopeptidase is a thermostable bacterial natural metallopeptidase derived from a strain of the genus *Geobacillus*.

10. The method of claim 1, wherein the alcohol is ethanol.

* * * * *